(12) United States Patent
Guest et al.

(10) Patent No.: US 7,666,177 B2
(45) Date of Patent: Feb. 23, 2010

(54) METHOD AND SYSTEM FOR CELLULAR TRANSPLANTATION IN THE SPINAL CORD

(75) Inventors: James Guest, 1095 NW. 14th Ter., Miami, FL (US) 33136; Carlos Casas, Miami, FL (US)

(73) Assignee: James Guest, Miami, FL (US)

( * ) Notice: Subject to any disclaimer, the term of this patent is extended or adjusted under 35 U.S.C. 154(b) by 0 days.

(21) Appl. No.: 10/940,131

(22) Filed: Sep. 14, 2004

(65) Prior Publication Data
US 2005/0085790 A1 Apr. 21, 2005

Related U.S. Application Data (60) Provisional application No. 60/503,134, filed on Sep. 15, 2003.

(51) Int. Cl.
*A61M 31/00* (2006.01)
(52) U.S. Cl. ...................... 604/506; 604/500
(58) Field of Classification Search ............. 604/500, 604/506, 508, 93.01; 606/100, 104, 105, 606/106
See application file for complete search history.

(56) References Cited

U.S. PATENT DOCUMENTS

| | | | | | |
|---|---|---|---|---|---|
| 4,904,237 | A | * | 2/1990 | Janese | 604/28 |
| 6,027,744 | A | * | 2/2000 | Vacanti et al. | 424/426 |
| 6,231,513 | B1 | * | 5/2001 | Daum et al. | 600/458 |
| 6,470,209 | B2 | * | 10/2002 | Snoke | 600/478 |
| 2002/0095124 | A1 | * | 7/2002 | Palasis et al. | 604/272 |
| 2002/0173796 | A1 | * | 11/2002 | Cragg | 606/86 |
| 2003/0014016 | A1 | * | 1/2003 | Purdy | 604/174 |
| 2004/0138621 | A1 | * | 7/2004 | Jahns et al. | 604/173 |

OTHER PUBLICATIONS

"Schwann cell genetically modified to secrete human BDNF promote axonal regowth across transected adult rat spinal cord". Phililppe Menei et al., European Journal of Neuroscience, vol. 10, pp. 607-621, 1998.*
Casas, CE, EJ Owen, Oliveira M, Guest JD: Endoscopic Transplantation into the conus medullaris. Soc. Neurosci Abstr. 2002 852.8. Nov. 2002.
Cellular transplantation into the spinal cord using an endoscopic technique. C Casas, E Owen, J Guest. Presented at the AANS/CNS Section on Disorders of the Spine and Peripheral Nerves, Orlando, FL, Feb. 2002.

* cited by examiner

*Primary Examiner*—Nicholas D Lucchesi
*Assistant Examiner*—Christopher D Koharski
(74) *Attorney, Agent, or Firm*—Fleit Gibbons Gutman Bongini & Bianco; Paul D. Bianco; Martin Fleit (57) ABSTRACT

The present invention provides a method for treating an injury of a spinal cord of a patient The method includes implanting a therapeutic substance in the spinal cord under indirect visualization. The indirect visualization may be provided by an endoscope, and the therapeutic substance may include cells. The present invention also provides a device for treating an injury of the spinal cord. The device includes skin visualization means for visualizing the spinal cord through a skin puncture, and injection means for injecting a therapeutic substance into the spinal cord.

36 Claims, 12 Drawing Sheets
(1 of 12 Drawing Sheet(s) Filed in Color)

METHOD AND SYSTEM FOR CELLULAR TRANSPLANTATION IN THE SPINAL CORD

CROSS-REFERENCE TO RELATED APPLICATION

The present application claims the benefit of U.S. provisional application no. 60/503,134 filed Sep. 15, 2003. The provisional application is hereby incorporated by reference.

FIELD OF THE INVENTION

The invention relates generally to a method and system for cellular transplantation, and in particular, to percutaneous endoscopic cellular transplantation into the spinal cord to create intramedullary cellular trails.

BACKGROUND OF THE INVENTION

Stereotaxic injection into the brain is facilitated by secure cranial immobilization in a stereotaxic frame. This has made it possible to accurately place transplants in the brain. However, stereotaxic injection into the spinal cord is more difficult due to the small size of the spinal cord, its constant motion in several planes relative to the vertebral spine, and its exquisite vulnerability to injury. For these reasons current spinal cord injection techniques rely upon direct visualization of the spinal cord during an open surgical procedure and immobilization of the spine in clamps during cellular injections. Since this type of surgical exposure is usually necessary to create an experimental spinal cord injury, various types of transplant techniques are possible using the same exposure.

Many spinal injuries require decompression and vertebral column stabilization surgery soon after hospitalization. This surgical opportunity may not be an optimal time for cellular injection to facilitate repair. Once this initial surgery has occurred, it is undesirable to disturb the progress of wound healing and bone fusion. Therefore, it is important to develop strategies of cell transplantation into the spinal cord compatible with minimal disturbance of the wound healing process. Cellular transplantation into the injured spinal cord has been used to study injury and repair responses in experimental models. Some clinical trials of cellular transplantation (e.g. activated macrophages, ensheathing glia) into the injured human spinal cord have been initiated using conventional open surgical techniques. Cell suspensions can be transplanted to create trails or columns of cells to partially reconstruct axonal pathways. In the spinal cord this requires either several closely spaced separate injections or a technique to enter the cord at a shallow angle. Currently, almost all injections into the spinal cord result in a tract defined by the needle path which is generally perpendicular to the longitudinal axis of the spinal cord.

There exists a need for a minimally invasive technique and system for cellular delivery in the spinal cord. Accordingly, the present invention provides a minimal access endoscope-assisted technique via a lumbar puncture approach without the need to create a large surgical incision. Cellular transplantation is performed under endoscopic visualization based on percutaneous access, remote from the injury site. Delivery of cells or cell suspension provides a trail of cells in the spinal cord which may span from the site of axonal injury to a useful target neuronal population. Regeneration of the damaged axons to the target neuron occurs via the transplanted supportive cells. The trail of cells is defined by the needle path which is generally parallel to the longitudinal axis of the spinal cord.

SUMMARY OF THE INVENTION

Spinal cord injections may be performed by introducing an endoscope percutaneously at an interlaminar space, for example a lumbosacral interspace. Because the epidural and subarachnoid spaces can be distended with fluid injection, endoscopic visualization of structures in these spaces can be achieved. The endoscope may be used with a syringe to inject a cellular suspension using a small catheter and endoscopically directed needle placed through the working channel of the endoscope. The system and method results in a columnar trail of transplant cells.

This strategy for intraspinal injection may confer important clinical advantages over other techniques. For example, using an endoscopic procedure instead of a CT-guided percutaneous technique, the spinal cord surface blood vessels can be visualized and avoided to prevent bleeding. Also, orientation to the midline is improved, and the depth of the needle insertion can be directly determined. As a further advantage, insertion of the endoscope at a non-injured site permits a cautious traversal of the endoscope from a normal region into the injury region of the spinal cord, thereby improving visual orientation. Also, the present invention eliminates the need for a laminectomy to access the spinal cord, facilitates flexibility of timing between surgical decompression and transplantation operations, reduces interference with healing of previous surgical incisions and fusion beds, facilitates multiple episodes of transplantation at different sites, reduces surgical duration, and may be performed under local anesthesia.

In accordance with one aspect of the present invention, there is provided a method for treating an injury of a spinal cord of a patient. The method includes implanting a therapeutic substance in the spinal cord under indirect visualization, such as an endoscope. The endoscope may be inserted through a skin puncture site remote from the injury of the spinal cord and through an interlaminar space of the patient, such as a lumbosacral interspace.

The method may further include inserting an injection member through the skin puncture site and into the spinal cord and injecting the therapeutic substance through an aperture of the injection member. The injection member may be at least partially withdrawn from the spinal cord while injecting the therapeutic substance to thereby form a trail of therapeutic substance. The injection member may be slideably disposed in a working channel of the endoscope and may include a needle connected to a catheter. The distal portion of the needle may be inserted into the spinal cord.

The method may also include reducing or damping motion of the needle in the spinal cord relative to the endoscope by providing a flexible portion of the catheter between the needle and a distal end of the endoscope. The therapeutic substance injected into the spinal cord may be cells, a cell suspension, or a biological matrix containing a therapeutic substance(s). The method may further include injecting distention fluid in the interlaminar space.

In an exemplary embodiment, the method may include the insertion of an implant into the patient. Use of percutaneous endoscopy may place syringopleural or cystoperitoneal cerebrospinal fluid (CSF) shunts within the spinal cord. Endoscopically-assisted shunting of intramedullary syringes, an arachnoid cyst, and/or a perineurial cyst may be performed.

In accordance with a similar aspect of the present invention, the injection member may include a catheter connected to a needle with a side-hole aperture. A flexible hollow guide wire may be positioned through the catheter and side-hole aperture of the needle and into the spinal cord. The therapeutic substance may be injected from the hollow guide wire while the guide wire is being withdrawn from the spinal cord to thereby form a trail of therapeutic substance in the spinal cord.

In accordance with another aspect of the present invention, a device is provided for treating an injury of the spinal cord of a patient. The device includes a visualization means for visualizing the spinal cord through a skin puncture located remote from the injury and an injection means for injecting a therapeutic substance into the spinal cord. The visualization means may be provided by an endoscope. The injection means may be withdrawn while injecting the therapeutic substance to thereby form a trail of therapeutic substance in the spinal cord. The device may also include means for fluid distention of an interlaminar space of the patient. Fluid distention facilitates endoscopic visualization because the optical density of the fluid permits illumination and visualization.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

The present invention provides a method and apparatus for making a percutaneous cellular injection into the spinal cord under endoscope visualization. The method includes percutaneously introducing a flexible endoscope into the subarachnoid space of the spinal cord, introducing a flexible catheter with an attached needle into a working channel or lumen of the endoscope, penetrating the spinal cord with the needle under direct visualization of the endoscope, and injecting cells into the spinal cord while the needle is withdrawn. The steps of penetrating the spinal cord and injecting cells into the spinal cord result in the implantation of a trail of cells within the spinal cord.

The system of the present invention provides for minimally invasive transplantation of cells within the spinal cord. A visualization means provides percutaneous viewing of the spinal cord (and/or interlaminar space, lumbosacral interspace, arachnoid, subarachnoid, pia mater). An injection means provides for the injection of cells into the spinal cord. The injection means may be configured for insertion through a working channel of the visualization means. The system provides a trail of implanted cells within the spinal cord.

Figure 1:
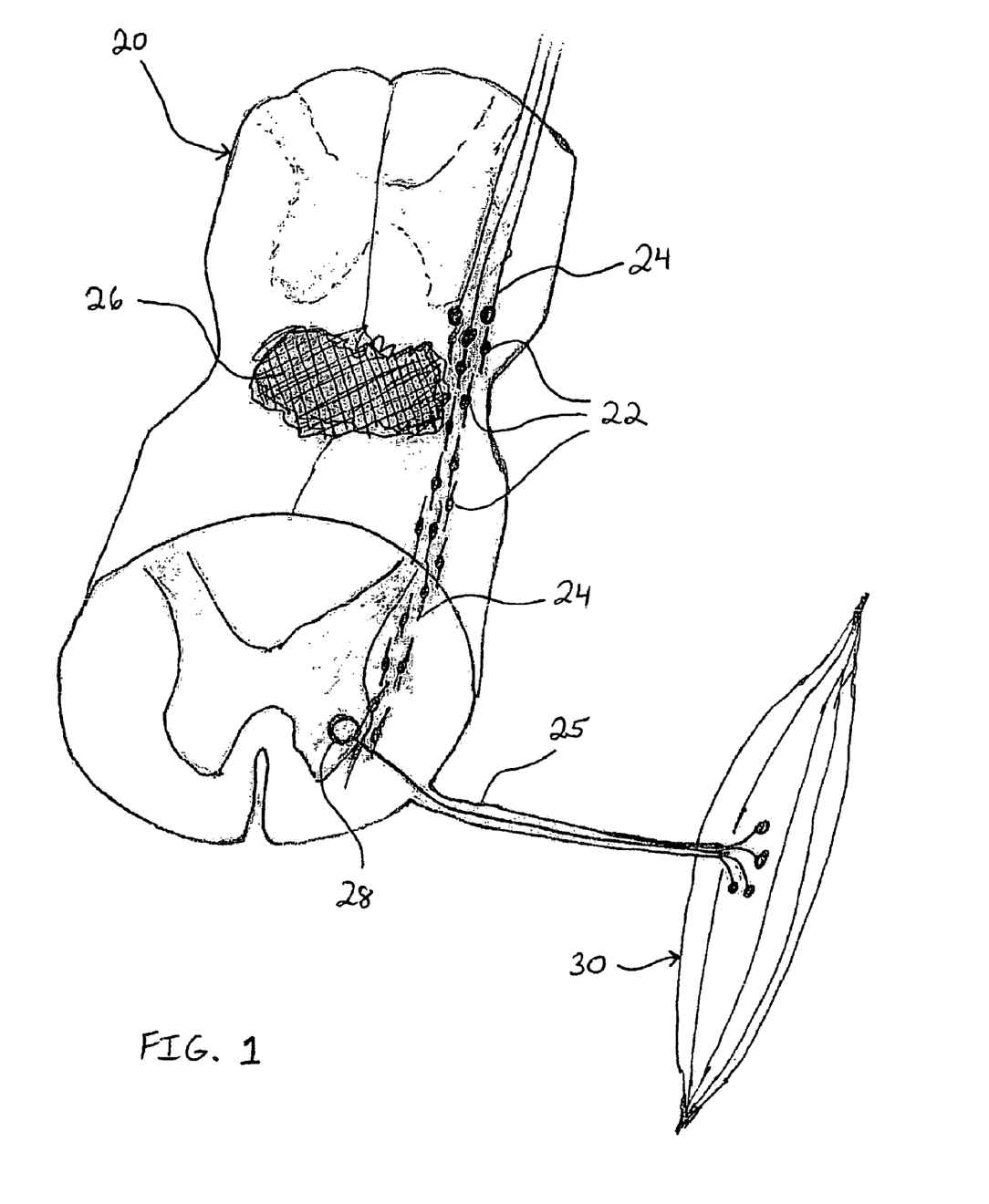
FIG. 1 illustrates a trail of cells implanted through a site of a spinal cord injury.

Referring now to FIG. 1, a portion of a spinal cord 20 having a trail of cells 22 implanted therein is illustrated. The cellular trail 22 may connect severed axons, neurons, and/or axons and neurons thereby leading to spinal cord repair. Severed axons 24 of a descending tract sprout and elongate along the trail of transplanted cells 22. The trail of cells 22 crosses an injured site 26 of the spinal cord 20 providing a bridge for axonal growth. The trail of cells 22 may allow regrowth to a target neuron 28 that sends axons 25 to an effector organ 30, such as a muscle. The transplanted cells may be implanted in a linear or non-linear configuration. Preferably, the trail of cells follows a path of the shortest distance between two connection points. However, the trail of cells may also take a curved or winding path. For example, an injured region of the spinal cord may prevent a linear trail of cells from being transplanted, so the trail of cells may curve around the injured region.

Figure 2:
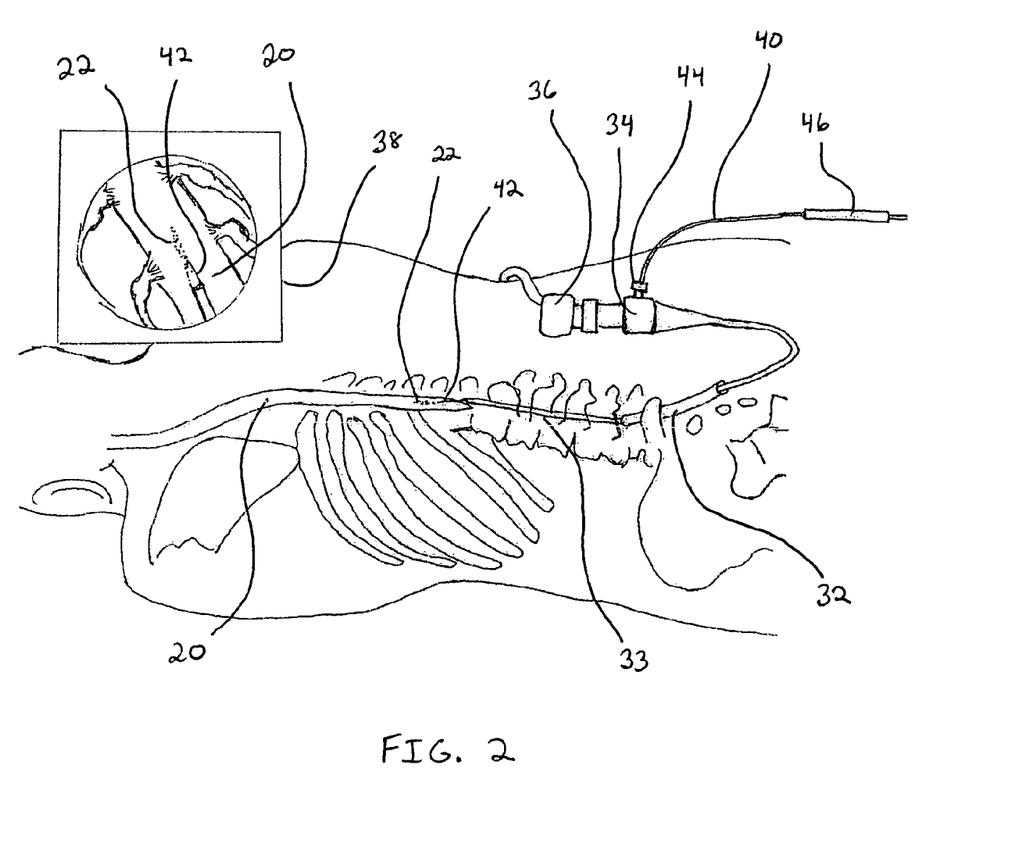
FIG. 2 illustrates an exemplary system for endoscopic cellular transplantation.

FIG. 2 illustrates an exemplary embodiment of the present invention. A cannula 32 is percutaneously positioned through the soft tissue near the spinal cord 20. The flexible distal portion 33 of an endoscope 34 is inserted through the cannula 32 so that the distal portion 33 of the endoscope 34 is in the interlaminar space, lumbosacral interspace, arachnoid, subarachnoid, and/or pia mater. The endoscope 34 is connected to a video camera 36, and an image of the spinal cord 20 can be seen on a monitor 38. An injection catheter 40 with a needle 42 enters the endoscope 34 through the working channel port 44. The distal portion of the needle 42 is placed into the spinal cord 20 at a specific location. The proximal portion of the injection catheter 40 is connected to a microsyringe 46. One mm marks or other indicia may be placed on the catheter 40 to enhance accuracy of catheter advancement.

Figure 3:
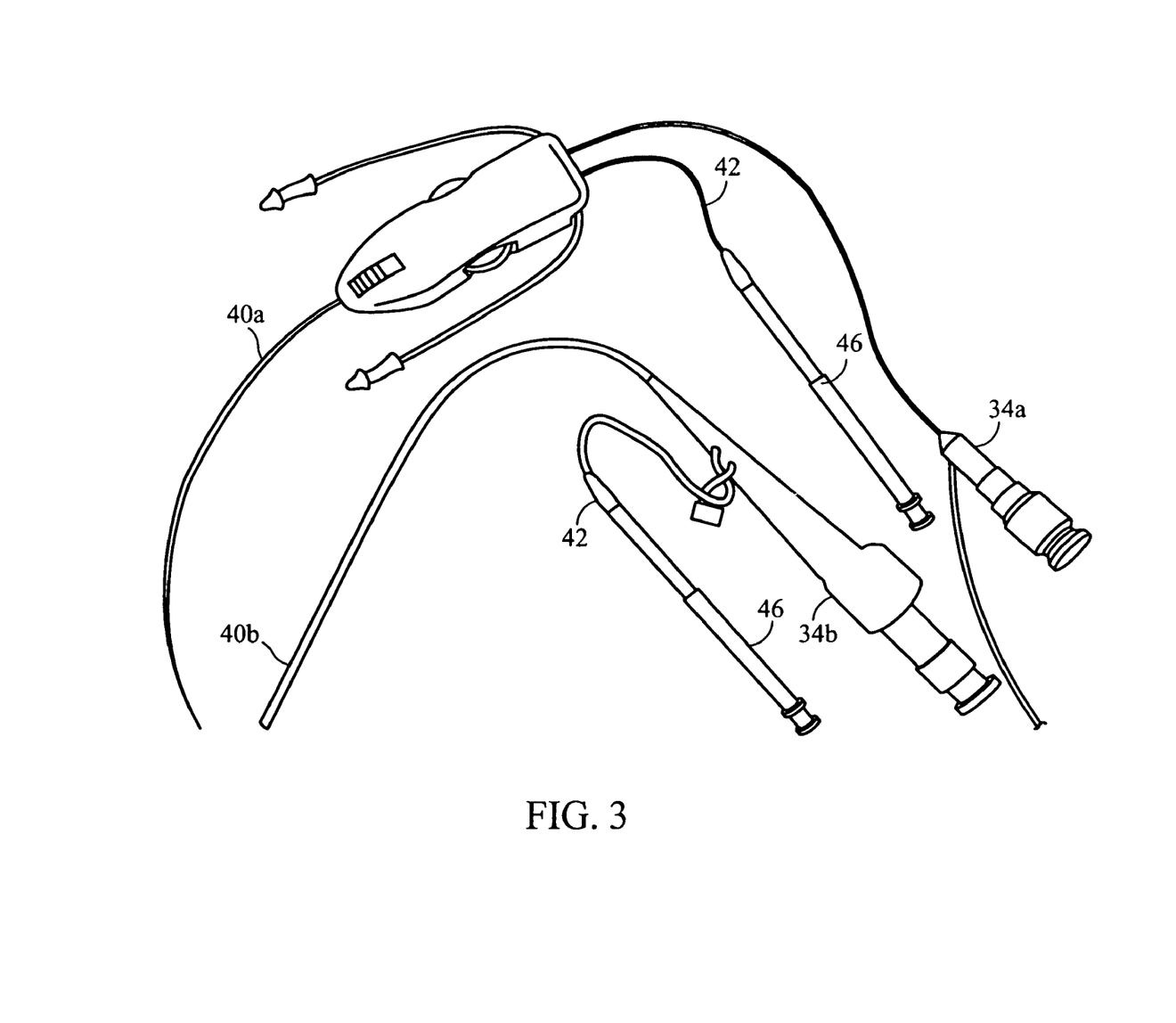
FIG. 3 shows exemplary endoscopes and related apparatus for use with the present invention.
Figure 3A:
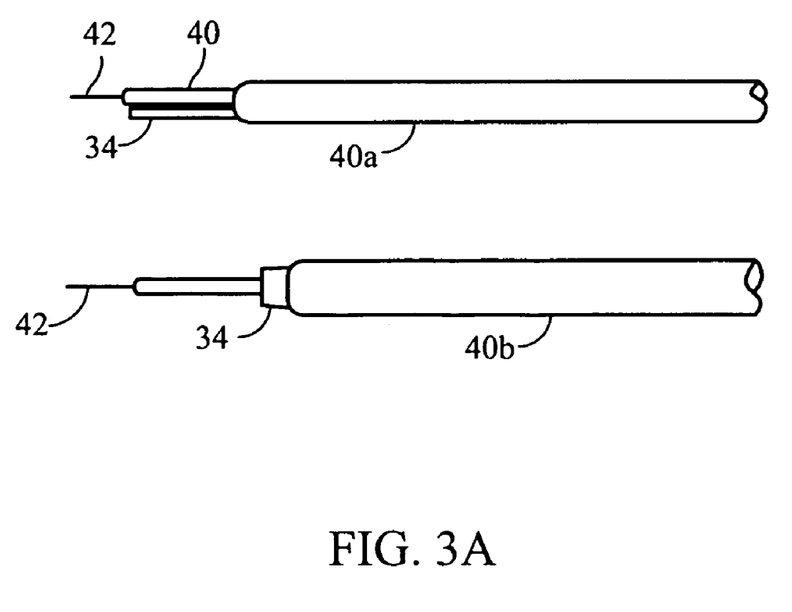
FIG. 3A is an expanded view of the distal ends of the endoscopes, catheters, and needles of FIG. 3.

FIGS. 3 and 3A illustrate two exemplary endoscopes for use in the present invention. It should be understood that any endoscope may be used with the present invention. Preferably, an endoscope with a working channel may be utilized. As seen in FIG. 3A, a MYELOTEC endoscope 34*a* includes a catheter module 35. A microsyringe 46 and catheter 40 are inserted into the catheter module 35. A CODMAN endoscope 34*b* is also shown. A microsyringe 46 and catheter 40 are inserted into the CODMAN endoscope 34*b*. As seen in FIG. 3A, the distal portion of the catheter module 35 is illustrated. The distal portion of the endoscope 34*a* is shown extended beyond the distal tip of the catheter module 35. The cell-filled catheter 40 and injection needle 42 are positioned in a working channel of the catheter module 35 and extend beyond the distal tip of the catheter module 35. The distal portion of the CODMAN endoscope 34*b* is shown with the cell-filled catheter 40 and injection needle 42 extended beyond the distal tip of the endoscope 34*b*. It is contemplated that other indirect visualization devices, such as MRI, CT scan, fluoroscopy, ultrasound, and X-ray, may be used with the present invention or used in combination with an endoscope.

Figure 4A:
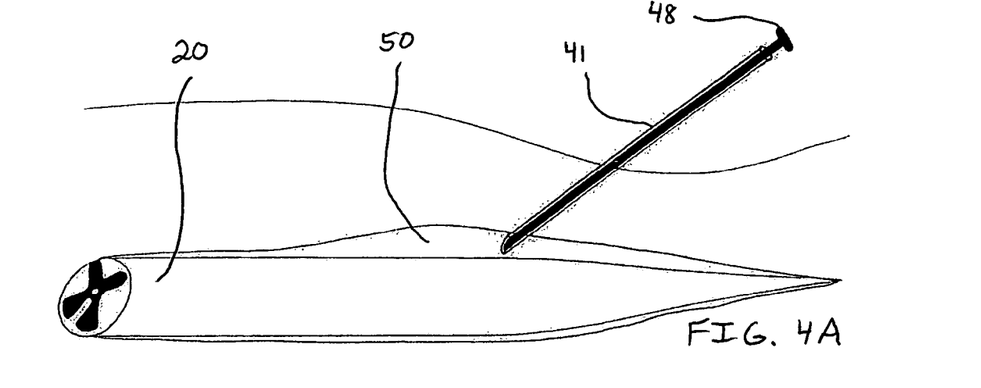
FIG. 4A shows a needle with a stylet positioned within the subarachnoid space of the patient.
Figure 4B:
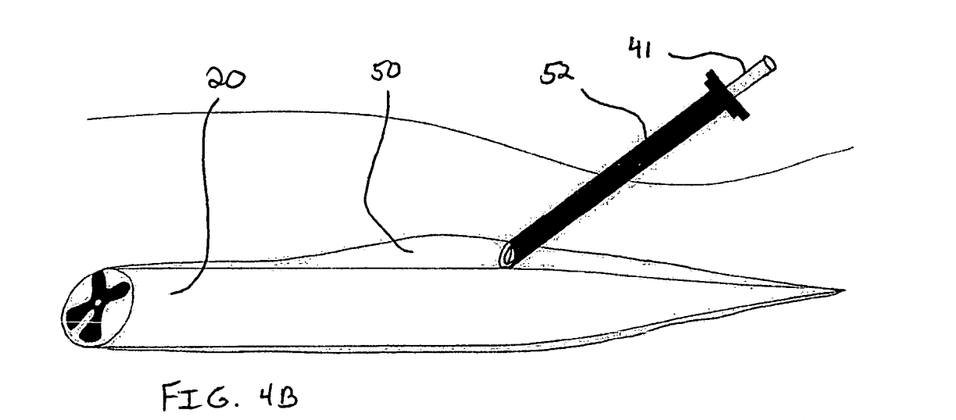
FIG. 4B shows an introducer placed over the needle.
Figure 4C:
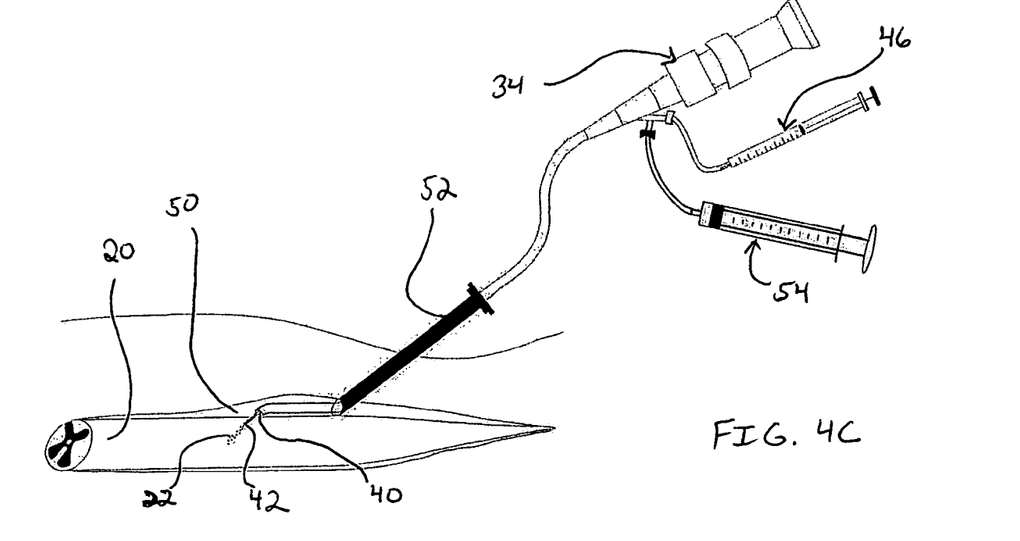
FIG. 4C shows an endoscope positioned in the introducer.

FIGS. 4A-4C illustrate an exemplary method of the present invention. A needle 41 with a stylet 48 is inserted through the patient's skin and into the subarachnoid space 50 of the spinal column. A peel-away introducer 52 is positioned over the needle 42 and inserted into the subarachnoid space 50. An endoscope 34 with a projecting catheter 40 and needle 42 is inserted into the introducer 52, and the distal portion of the endoscope 34 is inserted into the subarachnoid space 50. A syringe 46 containing cells and/or other therapeutic agent(s) is placed in fluid communication with the catheter 40 and needle 42. Using endoscopic visualization, the needle 42 is advanced distally to perforate the pia surrounding the spinal cord 20 and penetrate the spinal cord 20 to a desired depth. The syringe 46 is depressed pushing the cells and/or other therapeutic agent 22 into the spinal cord 20. If desired, while the cell suspension or other therapeutic agent is pushed from the syringe, the needle may be slowly withdrawn from the spinal cord to create a trail of cells. Furthermore, multiple rounds of transplantation could be performed at progressively distal sites to support regeneration over longer distances.

Another syringe 54 may be placed in fluid communication with the working channel of the endoscone 34. Distention fluid may be injected into the subarachnoid space 50 using the syringe 54.

In addition, the proximal end of the catheter may include indicia such as 1 mm marks to accurately determine how deep the needle has penetrated into the spinal cord. Also, a PE-10 polyethylene (or other suitable polymer) catheter may be used to hold the injection needle which may be a 30 G cut-down needle tip extending approximately 5 mm from the end of the injection catheter and set about 3 mm into the catheter. The PE-10 catheter may have an inner diameter of about 0.28 mm and a length of approximately 58 cm. As such, a volume of 35.7 μl of cell suspension may be pre-loaded into the catheter. The catheter may be back-filled with a cell suspension so that a continuous fluid column exists in the catheter. The continuous fluid within the catheter and syringe system provides uniform injection pressure thereby facilitating uniform cell dispersion.

The endoscope may be rotated after positioned in the subarachnoid space to optimize the relative positions of the optical and illumination fiber bundle, the working channel, and the dorsal spinal cord to perform the injection. Distention of the subarachnoid space with isotonic fluid may be useful prior to the injection since the endoscopic visualization is enhanced in a fluid filled space. The distention may be delivered by attaching tubing in fluid communication with the working channel of the endoscope so that fluid can be injected via the working channel beside the injection catheter. The fluid infusion pressure may be approximately 30-35 cm $H_2O$ and about 100 cc of fluid may be delivered during the procedure.

It is further contemplated that different injection parameters such as volume and injection rate may be utilized to minimize spilling the cell solution into the adjacent subarachnoid space. Also, distension fluid infusion may be stopped just before the cell injection is started to reduce the chance that the flow of fluid would cause cells to disperse from the injection site to other levels of the neuroaxis. Furthermore, the endoscope, catheter, and/or needle may be inserted through the patient's skin at a location distant from the cellular injection site. As an example, for a L1 level injury of the spinal cord conus medullaris, the endoscope is introduced at L5/S1 and then directed several centimeters rostral to the level just distal to the cord injury where the injection could be made provided the subarachnoid space was open. This increases the safety of the procedure by allowing the operator to become oriented to normal anatomic structures prior to entering the subarachnoid space surrounding the areas of spinal cord injury.

Figures 5A, 5B:
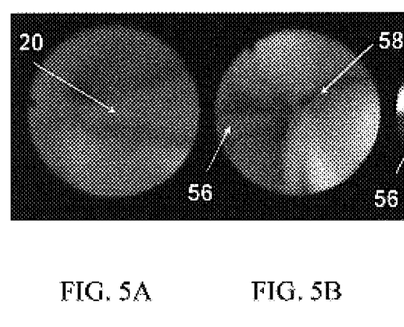
FIG. 5A is an endoscopic view of the dorsal spinal cord.
FIGS. 5B and 5C are endoscopic views of nerve roots and blood vessels of the spinal cord.
Figures 5C, 5D:
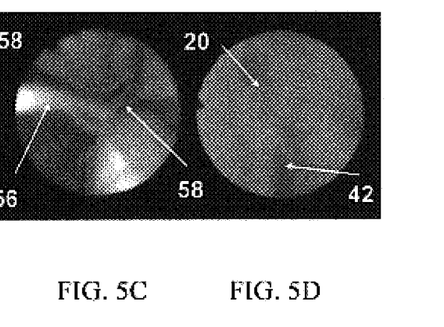
FIG. 5D is an endoscopic view showing a needle within the dorsal spinal cord.

FIGS. 5A-5D show images of the spinal cord as viewed from the endoscope. FIG. 5A shows a dorsal portion of the spinal cord 20. FIGS. 5B and 5C show nerve roots 56 and blood vessels 58 of the spinal cord 20. FIG. 5D illustrates the injection catheter with the needle 42 positioned within the dorsal spinal cord. In an exemplary embodiment, following pial perforation, the needle may be advanced by pushing the catheter into the endoscope working lumen. The cell suspension may be injected into the spinal cord, and the remainder may be injected while the needle is slowly withdrawn from the spinal cord over a period of time. Then, the needle may be left in position for another period of time before being withdrawn from the spinal cord parenchyma. Furthermore, by avoiding the extensive scarring associated with a laminectomy, the potential to perform multiple cell injections at progressively distal sites to support regeneration over a greater distance is facilitated.

Figure 6:
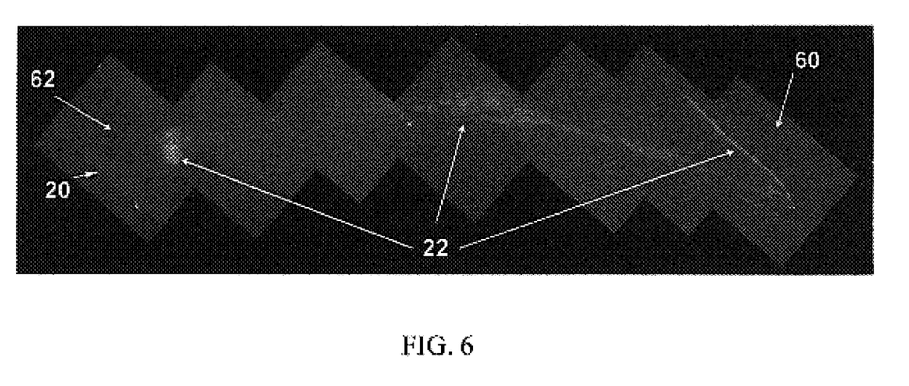
FIG. 6 is a fluorescent photomicrograph of a spinal cord section showing fluorescent fibroblasts after injection in the spinal cord.

FIG. 6 illustrates a trail of fluorescent fibroblasts 22 after endoscopic injection. The trail of fibroblasts 22 extend from the distal dorsal surface 60 of the spinal cord 20 to the ventral surface 62 of the spinal cord 20. It is further contemplated that iron oxide or other suitable contrast agent may be combined with the transplantation cells, cell suspension, or therapeutic agent. Using magnetic resonance imaging, the iron oxide may be visualized to thereby verify accurate implantation of the trail of cells. MRI visualization of the iron oxide and cells may be used during injection of the cells into the spinal cord as well as after implantation of the cells to ensure proper placement. Also, orientation of the injection system to the midline of the spinal cord may be facilitated by injections of small pulses of radiopaque contrast material. This technique helps establish that the injection needle is localized within the target site of the spinal cord, such as within a syringomyelic cavity.

Figures 7A, 7B:
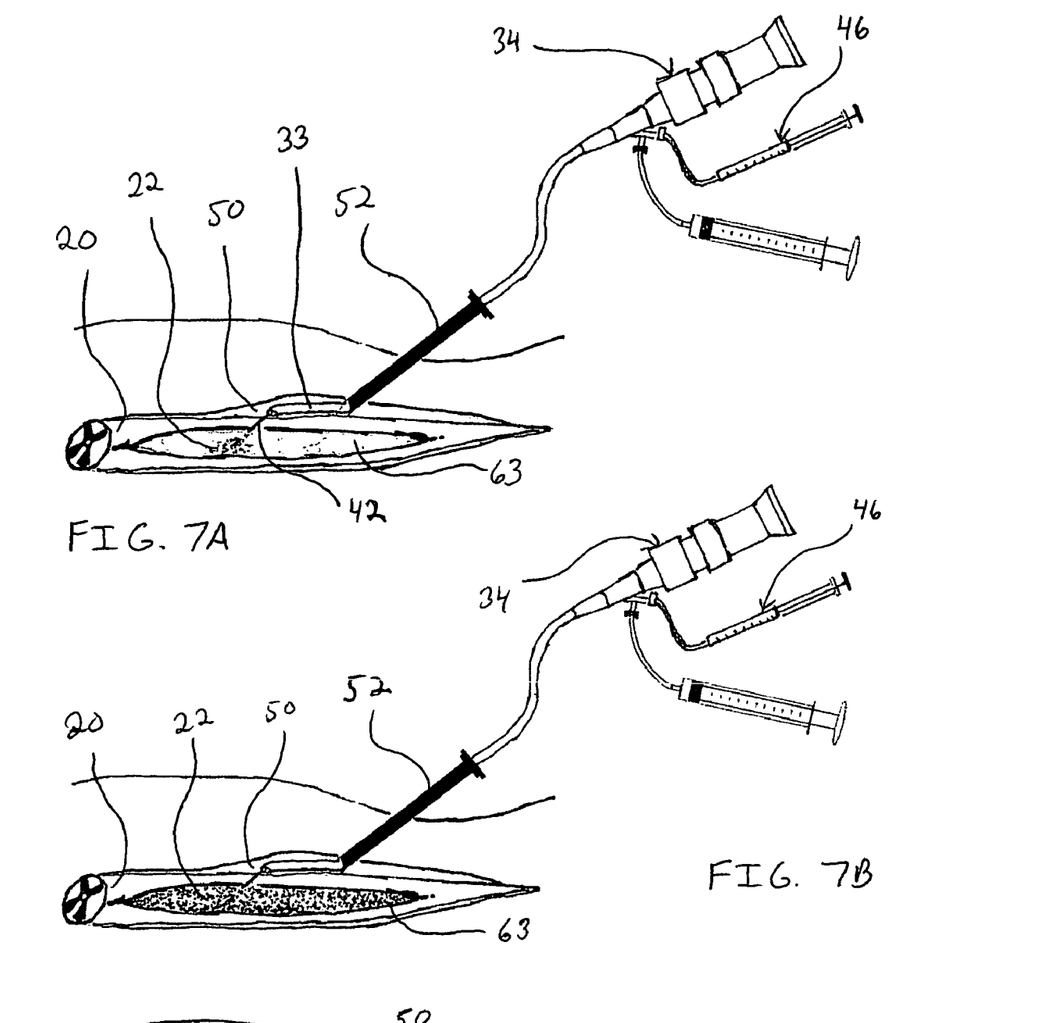
FIG. 7A shows a fluid filled cavity of an injured spinal cord being treated with transplanted cells.
FIG. 7B shows a large quantity of cells occupying the cavity.
Figure 7C:
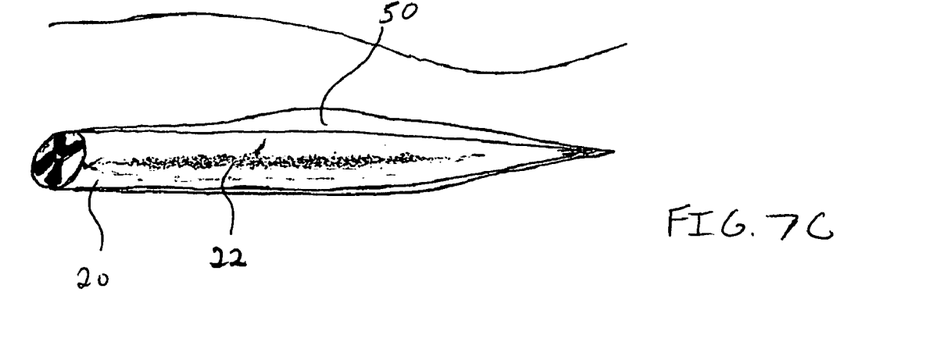
FIG. 7C shows a collapse of the fluid cavity after injection and integration of the cells.

Representing another exemplary embodiment of the present invention, FIGS. 7A-C illustrate treatment of syringomyelia disease within the spinal cord. FIG. 7A shows an introducer 52 positioned through the skin of a patient. An endoscope 34 is inserted through the introducer 52 with the flexible distal end 33 of the endoscope 34 placed into the subarachnoid space 50 of the spinal column. A syringe 46 containing cells and/or other therapeutic agent is placed in fluid communication with the catheter and needle 42. Using endoscopic visualization, the needle 42 is advanced distally to perforate the pia surrounding the spinal cord 20 and penetrate the spinal cord 20 to a desired depth within an expansile fluid-filled cavity 63 characteristic of syringomyelia. The syringe 46 is depressed pushing the cells 22 into the cavity 63 within the injured spinal cord 20. FIG. 7B shows a large quantity of transplanted cells 22 occupying the volume of the cavity 63. Following glial integration of the transplanted cells 22, the cavity 63 collapses, and there is no longer a progressive expansile fluid cavity 63, as seen in FIG. 7C.

Figure 8:
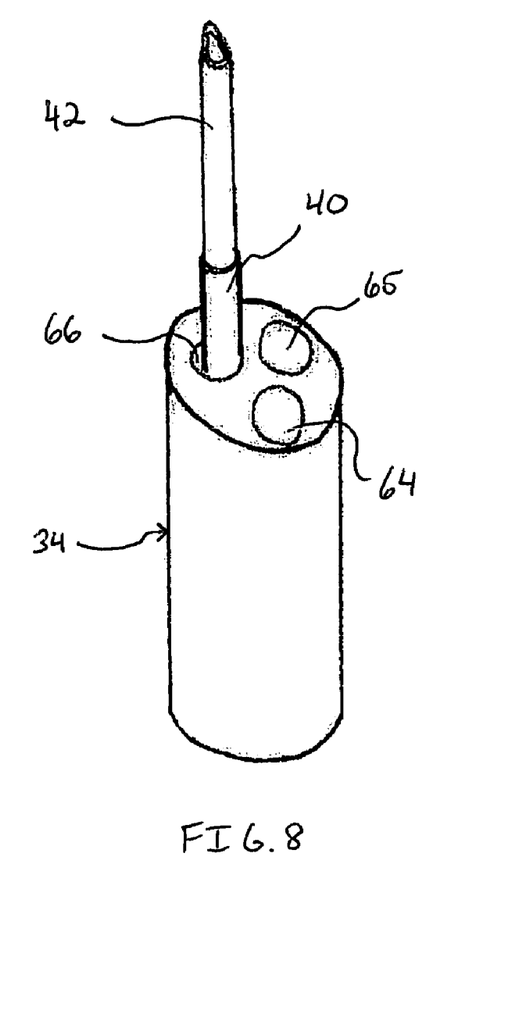
FIG. 8 illustrates the distal end of the endoscope with the catheter and needle disposed in the working channel of the endoscope.
Figure 9:
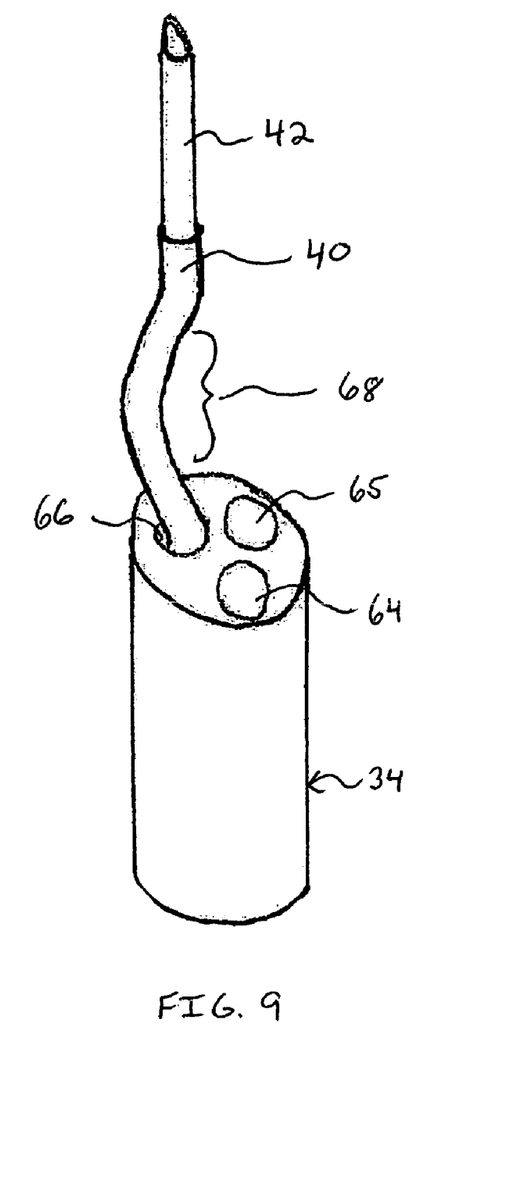
FIG. 9 illustrates the distal end of the endoscope with a flexible portion of the catheter positioned between the needle and endoscope.

Referring to FIGS. 8 and 9, the distal end of the endoscope 34 is illustrated. The endoscope 34 includes a lens or camera 64, an illumination bundle or rod 65, and a working channel or lumen 66. A catheter 40 is positioned within the working channel 66 of the endoscope 34. An injection needle 42 is inserted within the catheter 40. This configuration may provide the advantage that while the tubing 40 and needle 42 are partly within the endoscope working channel 66 they behave with similar rigidity to the endoscope 34, allowing controlled and accurate placement of the needle 42. As seen in FIG. 9, the device may be designed to minimize injection-related spinal cord trauma due to spinal cord motion relative to the needle 42 by using a segment of flexible tubing 68 between the endoscope 34 and the injection needle 42 to allow the needle 42 to move with the spinal cord during physiologic motion. Additionally, to facilitate this motion damping feature, the endoscope may be retracted while the needle is left in position within the spinal cord.

Figure 10:
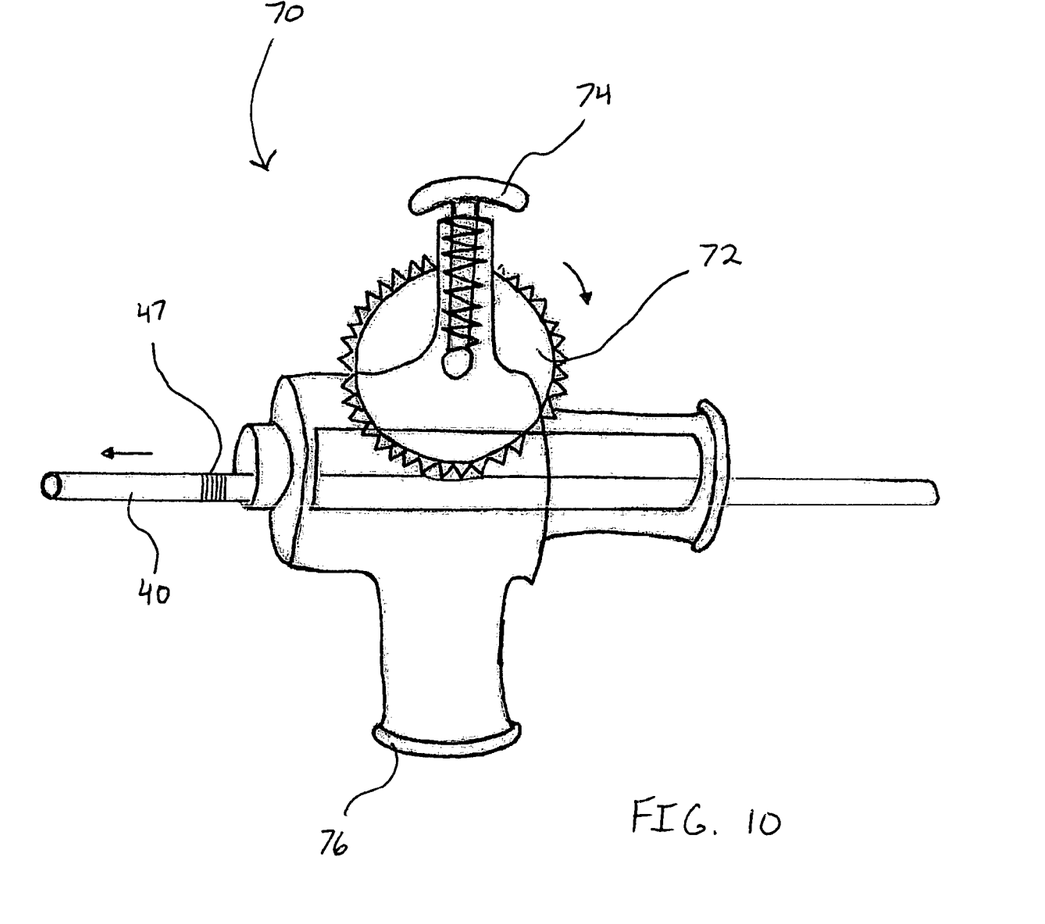
FIG. 10 illustrates a catheter advance device for use with the present invention.

FIG. 10 illustrates a three-way locking stopcock device 70 that can be used to control advancement of the catheter 40. A flexible injection catheter 40 is passed through the three way stopcock 70. A spring-loaded serrated wheel, gear, knob, cam, lever, etc. 72 can be rotated to advance the catheter 40 with a needle. The wheel 72 may be retracted in order to allow the endoscope to move relative to the needle and catheter 40. Using a button 74, the serrated wheel 72 can be pulled away from the flexible catheter 40 permitting the endoscope to be moved with respect to the catheter 40 after the needle is placed into the spinal cord, and also during advance of the catheter 40 through the endoscope. Using another port 76, fluid can be delivered to distend the subarachnoid space. Indicia such as 1 mm marks 47 may be placed on the catheter 40 to enhance accuracy of catheter advancement.

Figure 11:
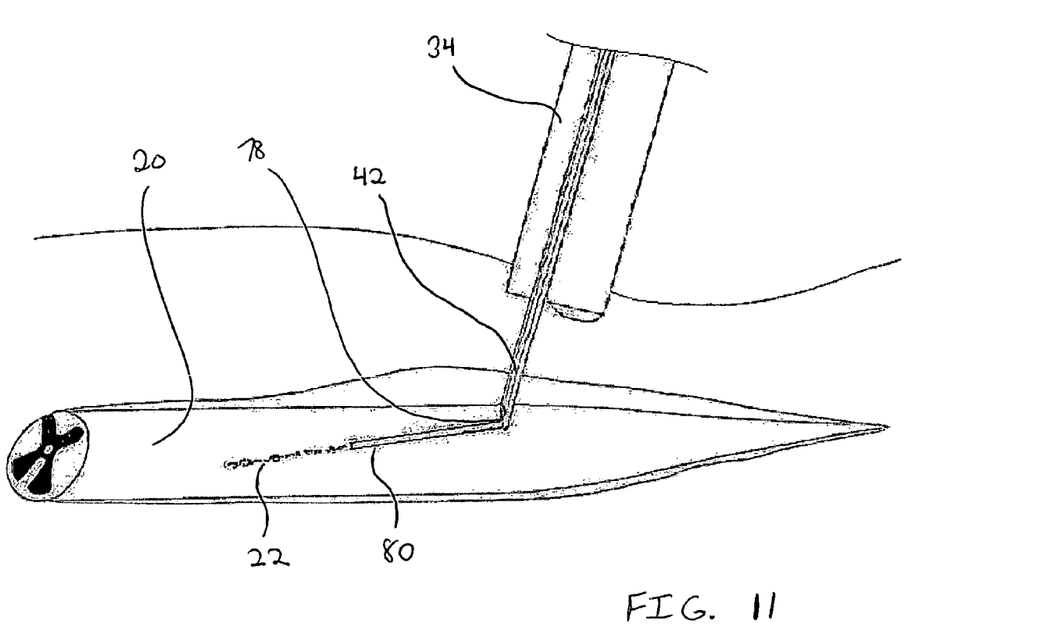
FIG. 11 illustrates another exemplary embodiment for cellular transplantation.

Referring to FIG. 11, a hollow needle 42 is attached to the polyethylene tubing, being inserted through the endoscope 34 working channel and advanced through the pia mater. The needle 42 includes a side-hole aperture 78, through which the flexible guidewire 80 is advanced out of the needle 42 into the spinal cord 20. The guidewire 80 may have sufficient stiffness to be advanced along a direction extending longitudinally from the side-hole aperture 78. In an exemplary embodiment, the needle 42 is a 30 gauge needle, and the guide wire 80 is a 0.0014" flexible, hollow guide wire dimensioned to advance out of the needle 42, through the side-hole aperture 78. The flexible hollow guide wire 80 is advanced for approximately 15 mm. The guidewire 80 follows a trajectory within the spinal cord 20 that is perpendicular to the side-hole needle 42. The extrusion of the cell trail 22 is commenced as the guidewire is slowly withdrawn.

Figure 12A:
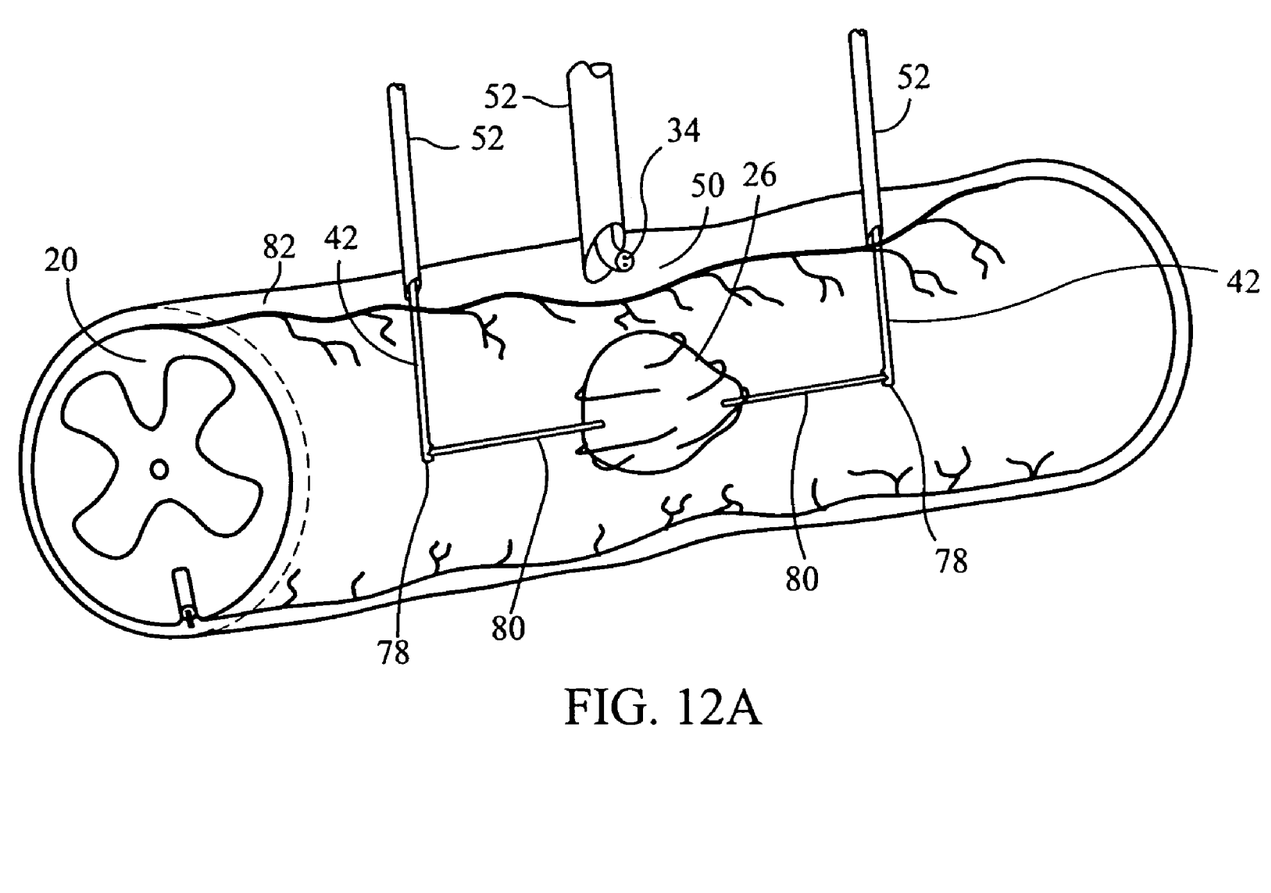
FIG. 12A illustrates an exemplary embodiment of the present invention with multiple percutaneous puncture sites.
Figure 12B:
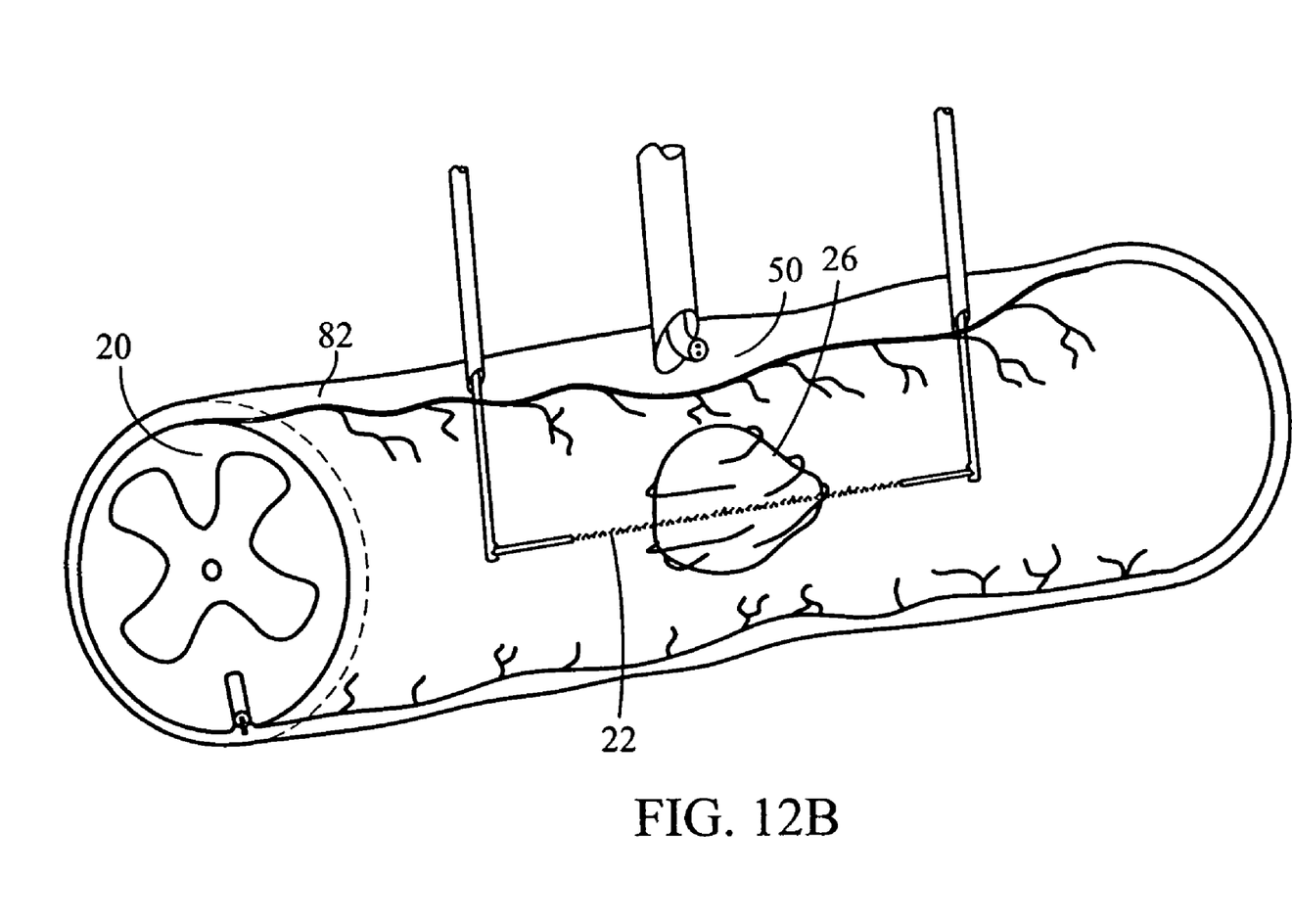
FIG. 12B illustrates a trail of cells transplanted within the spinal cord.

It is further contemplated that the catheter and needle may be positioned independent of the working channel of the endoscope. In FIG. 12A, the injection system and the endoscope are inserted into the patient by way of separate cannulas or introducers 52. The endoscope 34 is positioned through the skin and into the subarachnoid space 50. Using visualization from the endoscope 34, two separate side-hole injection needles 42 are deployed on generally opposite ends of an injured region 26 of the spinal cord 20. The injection needles 42 are positioned to avoid a large vein 82 of the dorsal spinal cord 20. Flexible hollow guidewires 80 extend through the side-hole apertures 78 and into the injured region 26. A cell suspension is ejected from the hollow guidewires 80 as the guidewires 80 are retracted back into the needles 42. As seen in FIG. 12B, a trail of cells 22 is formed extending through the injured region 26 of the spinal cord 20.

Clinical Trial

This study employed five cadaveric female pigs weighing approximately 30 kg.

NIH 3T3 fibroblasts were grown in DMEM with 10% fetal bovine serum in a tissue culture flask at 5% CO2 at 37° C. They were labeled with a fluorescent nuclear dye, Hoescht 33342 (Molecular Probes) at a concentration of 1:100. The cells were released from dishes using trypsin and triturated into a suspension. The cell suspension was then centrifuged at 1500 rpm for 5 minutes, the supernatant removed, and L-15 (Gibco) was added to achieve a final concentration of $10^5$ cells per µl. The cells were maintained on ice prior to injection.

The lumbosacral anatomy of the adult pig was studied to determine optimal entry points for percutaneous access to the spinal canal. The effectiveness of two flexible endoscopes was compared for this cell injection technique. The MYELOTEC fiberscope (Model 3000E) is designed for lumbar epidural procedures, and offers the advantage of small size (0.9 mm) but its tip is not independently steerable. The scope is deployed by insertion into a disposable 2.7 mm diameter catheter module (Model 4001) with dual Leur-lockable ports and channels. One channel is used to introduce the fiberscope, and the other can be used for irrigation or, for the present invention, insertion of the injection catheter. These ports provide some resistance to fluid back flow, and the introducer also has a valve to also resist fluid back flow. This is advantageous to reduce CSF loss and to maintain fluid distention of the CSF space. The device is "steered" by rotating a disc on the catheter module.

The other fiberscope that was studied was the CODMAN 83340 Neuroguide IOVS. It is a 38 cm long steerable scope of 3.2 mm diameter with a 3 FR working channel. It has a tip articulation of 100-160 degrees, the depth of field is 5-50 mm, and the field of view is 64 degrees in water. Both scopes were deployed in all five animals. For this trial, however, the CODMAN 83340 scope was used for the cellular injections. The endoscopes were coupled to a high resolution color CCD camera (Endoview, Urohealth Systems Inc., Costa Mesa, Calif.). One video output signal was connected to a monitor, and the second output signal was used to acquire digital video using a Sony DCR-PC100 digital video camera.

To access the lumbar subarachnoid space with the MYELOTEC fiberscope, a 14 G spinal needle (2.1 mm OD) was directed between L5 and L6, 7 cm rostral to the sacral depression until there was loss of resistance in a glass syringe (epidural space). Next, the dura was penetrated and CSF returned and the depth in mm from the skin to the dural opening was measured. A flexible guidewire was placed through the needle into the subarachnoid space (SAS). The spinal needle was removed and the 7F introducer sheath (2.33 mm OD) was advanced over the guidewire. The guidewire was removed and the catheter module introduced. Next, the 0.9 mm (OD) fiberscope was advanced through the catheter module until emergence and visualization of nerve roots was detected. Pulsatile injection of saline through the second channel improved image quality and made it easier to navigate the catheter module and endoscope.

Placement of the CODMAN scope was different than the MYELOTEC fiberscope because of its greater size. A 12.5F peel-away introducer was fed over a large (10 G, OD=3.4 mm) needle placed into the SAS at L5/6. The needle was then removed and the endoscope introduced into the SAS through the sheath. A large syringe (30 cc) was attached via a three-way stopcock to the working channel port and small pulses of saline were injected. Both endoscopes were navigated adjacent to the dorsal or dorsolateral spinal cord surface. Because the CODMAN introducer does not have a valve to prevent backflow, more fluid was used to distend the subarachnoid space since there was a constant loss of fluid through the small gap between the scope and the introducer.

All cellular injections described hereinafter were delivered using the CODMAN endoscope. Injection was performed in a dorsal midline area at the L2 vertebral level. Thirty-six µl of the cell suspension was loaded into a polyethylene tube [0.61 mm OD, 0.28 mm ID] 58 cm in length (Intramedic polyethylene tubing PE-10) with a 30 G needle (8 mm total length, OD 0.3 mm) attached at its distal end. Fluid infusion was stopped, and the catheter was slowly inserted into the working channel and advanced distally until the needle tip could be visualized to exit the endoscope. It was then necessary to rotate the endoscope to optimize the relative positions of the optical fiber bundle, the needle, and the dorsal spinal cord. With the scope facing the dorsal spinal cord surface at a 45 degree angle, the needle was advanced until it contacted the pial surface.

Following pial perforation, the needle was advanced 4 mm along a rostro-ventral trajectory by gently pushing the catheter into the endoscope. At this point irrigation was terminated with the subarachnoid space moderately distended at a pressure of 30-35 cm $H_2O$. One µl of cell suspension was injected, and another 4 ul was injected while the needle was slowly withdrawn from the cord over about 5 minutes. Then, the needle was left in position for a further two minutes before being removed from the spinal cord parenchyma. No further pulses of saline irrigation were delivered in order to minimize the possibility of flushing the cells along the neural axis. The endoscope was removed and 4% paraformaldehyde was slowly infused into the subarachnoid space around the injection site. A lumbar laminectomy was then performed to remove the injected region of the spinal cord for histological evaluation.

In preparation for histological assessment, the specimens were post-fixed in 4 percent paraformaldehyde for two weeks. The cord was embedded in gelatin and cut into 55 µm sagittal sections using a sliding freezing microtome. The sections were visualized using a Zeiss Axiophot fluorescent microscope to identify the fluorescent-labeled injected cells. Digital images were acquired at 10× using METAMORPH software. Image montages were constructed in ADOBE PHOTOSHOP 5.0 to show the full length of the cellular trail within the spinal parenchyma and to assess for spillage at the adjacent spinal cord margins.

A useful anatomic landmark in the pig is a palpable sacral depression (SD) from which the L5/6 interspace was located 7 cm rostrally. The vertical distance from the skin to the dorsal surface of the cord at L5/6 was 6-7 cm. The interlaminar spaces (or lumbosacral interspaces) at L5-6 and L6-S1 at the midline were 4.0 and 2.5 mm respectively. The porcine conus medullaris terminates within the sacrum 3 cm rostral to the SD, thus there is no true lumbar cistern as in the human.

Video image quality was similar using either the MYELOTEC or CODMAN endoscopes. Blood vessels, nerve roots, and denticulate ligaments could be visualized with either endoscope. Adequate visualization of anatomic details during scope navigation required pulsatile irrigation of the subarachnoid space with fluid. Although the size of the CODMAN scope was greater, the ability to control the direction of the injection needle and catheter was better than with the disposable MYELOTEC catheter module. This appeared to be due to stiffness within the scope tip and the fact that the CODMAN scope was only actively directable at the tip. The steering motion of the MYELOTEC scope was more whip-like and it tended to flip from the midline to the lateral spinal canal during attempted injections. For this reason, the CODMAN endoscope was utilized for definitive injections.

A useful feature of this technique is that while the tubing and at least part of the needle are within the scope, the needle behaves as a rigid extension of the scope. This allows for the force necessary to penetrate the pial surface. When a loop of tubing is fed out between the tip of the scope and the needle after insertion into the cord, small motions of the scope and spinal cord are damped with respect to the needle. This has the effect of reducing injection-associated spinal cord trauma by allowing the needle to move with the spinal cord during physiologic motion.

Trial Results

During histological analysis, a trail of Hoechst-labeled cells was identified in each specimen under a fluorescent microscope. Some trails were homogenously distributed whereas others consisted of interspersed clumps of labeled cells. Some cell spillage was evident on the adjacent pia in 4/5 specimens; however, cells were not seen more than 3 mm from the injection site, and neither traumatic distention of the central canal nor cavitation as a result of the injection was observed.

The development of small flexible fiberoptic scopes and high resolution CCD cameras has lead to increased interest in the use of endoscopes for spinal canal applications. Multiple injections into the spinal cord over an extended time period may be necessary for effective regeneration. The technique described herein could also be used to deliver non-cellular biomaterials into the subarachnoid space or spinal cord. Alternatively, other therapeutic effects, such as pain modulation via chromaffin cells transplanted into the subarachnoid space might be achieved with this technique.

Due to camera and display interface associated degradation, an alternative consideration is to use rigid endoscopes with their superior rod lens optics. A technique based on a rigid endoscope would sacrifice some of the advantages of the flexible scope such as entry into the subarachnoid space at a point several segments distal to the injection site and the flat injection trajectory possible by having the flexible scope nearly parallel to the spinal cord. The incorporation of backflow resistance valves into the MYELOTEC introducer and catheter module means that less fluid volume needs to be delivered to distend the subarachnoid space than with the CODMAN introducer where some constant backflow occurs. However, the advantage of not incorporating a valve is that CSF pressures are less likely to be escalated using the CODMAN introducer and endoscope. Using a porcine model of subdural fluid infusion, it has been shown that spinal cord ischemia occurs at induced CSF pressures of approximately 65 mm Hg.

While dural puncture is simple with a spinal needle, getting flexible introducers to enter the porcine dural sheath over a guidewire requires more effort. Therefore, a large spinal needle was used to improve the ability to pass the CODMAN guide sheath through the dura. In clinical application of the 7F MYELOTEC introducer for intradural procedures, there have not been CSF leaks.

The concept of creating cellular trails to guide regenerating axons assumes that cellular migration following transplantation is minimal. Random cellular migration could lead to poorly organized or misdirected axonal growth. In a previous study trails of Schwann cells were not dispersed 6 weeks after injection. Axons grew along the trails in a fasciculated pattern similar to that seen in peripheral nerve grafts. The injection technique utilized in this trial appeared to cause little injury to the spinal cord.

Percutaneous endoscopic cellular injection may be useful for cellular transplantation, may reduce surgical and anesthetic time, be compatible with local anesthesia, eliminate the need to disrupt spinal instrumentation and bone grafts, and allow greater flexibility in the respective timing of spinal fixation and cellular transplantation following spinal cord injury. Using the system and method according to the present invention, intraspinal cellular injection using a flexible endoscope from a percutaneous access is achievable.

All references cited herein are expressly incorporated by reference in their entirety.

It will be appreciated by persons skilled in the art that the present invention is not limited to what has been particularly shown and described herein above. In addition, unless mention was made above to the contrary, it should be noted that all of the accompanying drawings are not to scale. Accordingly, a variety of modifications and variations are possible in light of the above teachings without departing from the scope and spirit of the invention. For example, the invention has been described with reference to a spinal cord procedure. It should be appreciated that the present invention can be applied to a number of situations in which percutaneous introduction of cells or other biomaterial is desired.

What is claimed is:

1. A method for treating an injury of a spinal cord of a patient comprising:
    inserting an endoscope, including a catheter with a needle attached to a distal end, through a skin puncture;
    moving a distal portion of the endoscope into a subarachnoid space of the spinal cord;
    placing at least one syringe in fluid communication with the catheter and needle, wherein the syringe contains a fluid for distension of the subarachnoid space;
    depressing the syringe to release the fluid thereby distending the subarachnoid space;
    visualizing the spinal cord through the skin puncture;
    advancing the needle in the subarachnoid space;
    perforating a pia surrounding the spinal cord with the needle;
    stopping release of the fluid from the syringe;
    injecting a therapeutic substance from the needle into the spinal cord; and
    withdrawing the needle over a period of time creating a trail of therapeutic substance parallel to a longitudinal axis of the spinal cord.

2. The method according to claim 1, further comprising inserting an introducer into the subarachnoid space prior to insertion of the endoscope, wherein the endoscope is then inserted through the introducer.

3. The method according to claim 1, wherein the needle is slidably disposed in a working channel of the endoscope.

4. The method according to claim 1, wherein the catheter further includes a flexible portion between the needle and a distal end of the endoscope.

5. The method according to claim 1, wherein injecting the therapeutic substance includes injecting the therapeutic substance through an aperture of the needle.

6. The method according to claim 1, wherein a magnetic resonance reflective material is injected with the therapeutic substance.

7. The method according to claim 6, wherein injecting the therapeutic substance is performed under magnetic resonance imaging.

8. The method according to claim 1, wherein the therapeutic substance includes cells.

9. The method according to claim 8, wherein the skin puncture is remote from the injury of the spinal cord.

10. The method according to claim 9, wherein the trail of cells crosses the injury of the spinal cord between two connection points along the longitudinal axis of the spinal cord, wherein one connection point is proximal to the injury and the other connection point distal to the injury, wherein said trail provides a bridge for growth of new axons and new neurons through the injury.

11. The method according to claim 10, wherein the trail of cells connects severed axons, severed neurons, or both severed axons and neurons.

12. A method for treating an injury of a spinal cord of a patient comprising:
    inserting an endoscope, including a catheter with a needle attached to a distal end, through a skin puncture;
    moving a distal portion of the endoscope into a subarachnoid space of the spinal cord;
    placing at least one syringe in fluid communication with the catheter and needle, wherein the syringe contains a fluid for distension of the subarachnoid space;
    depressing the syringe to release the fluid thereby distending the subarachnoid space;
    visualizing the spinal cord through the skin puncture;
    advancing the needle into the subarachnoid space;
    perforating a pia surrounding the spinal cord with the needle;
    moving a hollow guidewire through the needle;
    stopping release of the fluid from the syringe;
    injecting a therapeutic substance from the hollow guidewire into the spinal cord; and
    withdrawing the guidewire over a period of time creating a trail of therapeutic substance parallel to a longitudinal axis of the spinal cord.

13. The method according to claim 12, wherein the needle includes a side-hole aperture.

14. The method according to claim 13, wherein moving the hollow guidewire through the needle includes moving the hollow guidewire in a direction extending longitudinally from the side-hole aperture of the needle.

15. The method according to claim 12, wherein the therapeutic substance includes cells.

16. The method according to claim 15, wherein the skin puncture is remote from the injury of the spinal cord.

17. The method according to claim 16, wherein the trail of cells crosses the injury of the spinal cord between two connection points along the longitudinal axis of the spinal cord, wherein one connection point is proximal to the injury and the other connection point distal to the injury, wherein said trail provides a bridge for growth of new axons and new neurons through the injury.

18. The method according to claim 17, wherein the trail of cells connects severed axons, severed neurons, or both severed axons and neurons.

19. A method for treating an injury of a spinal cord of a patient comprising:
    inserting an endoscope, including a catheter with a needle attached to a distal end, through a skin puncture;
    moving a distal portion of the endoscope into a subarachnoid space of the spinal cord;
    delivering a fluid through a port in the endoscope thereby distending the subarachnoid space;
    visualizing the spinal cord through the skin puncture;
    advancing the needle in the subarachnoid space;

perforating a pia surrounding the spinal cord with the needle;

stopping release of the fluid from the port;

injecting a therapeutic substance from the needle into the spinal cord; and withdrawing the needle over a period of time creating a trail of therapeutic substance parallel to a longitudinal axis of the spinal cord.

20. The method according to claim 19, further comprising inserting an introducer into the subarachnoid space prior to insertion of the endoscope, wherein the endoscope is then inserted through the introducer.

21. The method according to claim 19, wherein the needle is slidably disposed in a working channel of the endoscope.

22. The method according to claim 19, wherein the catheter further includes a flexible portion between the needle and a distal end of the endoscope.

23. The method according to claim 19, wherein injecting the therapeutic substance includes injecting the therapeutic substance through an aperture of the needle.

24. The method according to claim 19, wherein a magnetic resonance reflective material is injected with the therapeutic substance.

25. The method according to claim 24, wherein injecting the therapeutic substance is performed under magnetic resonance imaging.

26. The method according to claim 19, wherein the therapeutic substance includes cells.

27. The method according to claim 26, wherein the skin puncture is remote from the injury of the spinal cord.

28. The method according to claim 27, wherein the trail of cells crosses the injury of the spinal cord between two connection points along the longitudinal axis of the spinal cord, wherein one connection point is proximal to the injury and the other connection point distal to the injury, wherein said trail provides a bridge for growth of new axons and new neurons through the injury.

29. The method according to claim 28, wherein the trail of cells connects severed axons, severed neurons, or both severed axons and neurons.

30. The method according to claim 29, wherein the therapeutic substance includes cells.

31. The method according to claim 30, wherein the skin puncture is remote from the injury of the spinal cord.

32. The method according to claim 31, wherein the trail of cells crosses the injury of the spinal cord between two connection points along the longitudinal axis of the spinal cord, wherein one connection point is proximal to the injury and the other connection point distal to the injury, wherein said trail provides a bridge for growth of new axons and new neurons through the injury.

33. The method according to claim 32, wherein the trail of cells connects severed axons, severed neurons, or both severed axons and neurons.

34. The method according to claim 19, further comprising:

moving a hollow guidewire through the needle;

stopping release of the fluid from the port;

injecting a therapeutic substance from the hollow guidewire into the spinal cord; and withdrawing the guidewire over a period of time creating a trail of therapeutic substance parallel to a longitudinal axis of the spinal cord.

35. The method according to claim 34, wherein the needle includes a side-hole aperture.

36. The method according to claim 35, wherein moving the hollow guidewire through the needle includes moving the hollow guidewire in a direction extending longitudinally from the side-hole aperture of the needle.

* * * * *